(12) United States Patent
Brocia

(10) Patent No.: US 10,495,652 B1
(45) Date of Patent: Dec. 3, 2019

(54) DETERMINATION OF LCAT

(71) Applicant: Roar Holding LLC, New York, NY (US)

(72) Inventor: Robert W. Brocia, Bronxville, NY (US)

(73) Assignee: Roar Holding LLC, New York, NY (US)

( * ) Notice: Subject to any disclaimer, the term of this patent is extended or adjusted under 35 U.S.C. 154(b) by 0 days.

(21) Appl. No.: 14/656,120

(22) Filed: Mar. 12, 2015

Related U.S. Application Data

(63) Continuation of application No. 13/862,296, filed on Apr. 12, 2013, now abandoned.

(60) Provisional application No. 61/624,191, filed on Apr. 13, 2012, provisional application No. 61/642,337, filed on May 3, 2012.

(51) Int. Cl.
| | | |
|---|---|---|
| *G01N 33/92* | (2006.01) | |
| *C12Q 1/48* | (2006.01) | |
| *C12Q 1/60* | (2006.01) | |
| *G01N 33/58* | (2006.01) | |

(52) U.S. Cl.
CPC ............ *G01N 33/92* (2013.01); *C12Q 1/48* (2013.01); *C12Q 1/60* (2013.01); *G01N 33/582* (2013.01); *G01N 2333/91057* (2013.01); *G01N 2405/00* (2013.01)

(58) Field of Classification Search
None
See application file for complete search history.

(56) References Cited

U.S. PATENT DOCUMENTS

| | | | |
|---|---|---|---|
| 4,184,921 A | | 1/1980 | Roeschlau et al. |
| 5,063,070 A | * | 11/1991 | Klemann ............... A23L 1/0156 210/679 |
| 5,122,454 A | * | 6/1992 | Ueda ........................ C12Q 1/60 435/11 |
| 6,635,614 B1 | * | 10/2003 | Santamarina-Fojo ...................... A01K 67/0278 435/320.1 |
| 2009/0074740 A1 | * | 3/2009 | Berkowitz ........... C12Q 1/6883 424/94.4 |
| 2009/0137544 A1 | | 5/2009 | Li |
| 2010/0330604 A1 | | 12/2010 | Labarthe et al. |

FOREIGN PATENT DOCUMENTS

| | | |
|---|---|---|
| EP | 1164376 | 12/2001 |

OTHER PUBLICATIONS

Francone et al., Expression of Human Lecithin-Cholesterol Acyltransferase in Transgenic Mice, J. Clin. Invest. 96, (1995), p. 1440-1448.*
Biotek Application Note (Held, Paul. (2005) Quantitation of Cholesterol using a Fluorometric Assay and the SynergyTMHT Multi-Detection Microplate Reader (Application Note), 5 pages (Year: 2005).*
Schroeder et al., Fluorometric Evidence for the Binding of Cholesterol to the Filipin Complex, The Journal of Antibiotics, XXIV(12), (1971), p. 846-849 (Year: 1971).*
Schroeder et al., Fluorometric Investigations of the Interaction of Polyene Antibiotics with Sterols, Fluorescence properties of filipins, 11(16), (1972), p. 3105-3111 (Year: 1972).*
Albers et al., "Radioimmunoassay of Human Plasma Lecithin-cholesterol acyltransferase," J. Clin. Invest. (1981) 67:141-148.
Bittman et al., "Fluoescence studies of the binding of the polyene antibiotics filipin III, amphotericin B, nystatin, and Lagosin to cholesterol," Proc. Nat. Acad. Sci. (1972) 69(12):3795-3799.
McPherson et al., "High density lipoprotein subfractions: isolation, composition, and their duplicitous role in oxidation," Journal of Lipid Research (2007) 48:86-95.
Muller et al., "Filipin as a flow microfluorometry probe for cellular cholesterol," Cytometry (1984) 5(1):42-54.
Hassal and Graham, "Changes in free cholesterol content, measured by filipin fluorescence and flow cytometry, correlate with changes in cholesterol biosynthesis in THP-1 macrophages," Cytometry (1995) 21(4):352-362.

* cited by examiner

*Primary Examiner* — Christine Foster
*Assistant Examiner* — Ellen J Marcsisin
(74) *Attorney, Agent, or Firm* — Morrison & Foerster LLP

(57) ABSTRACT

Advantage is taken of macrolide antibiotics' complexation with free cholesterol to yield fluorescent complexes to determine the levels of free cholesterol, total cholesterol, or lecithin: cholesterol acyl transferase (LCAT) in serum or plasma or fractions thereof.

4 Claims, 1 Drawing Sheet

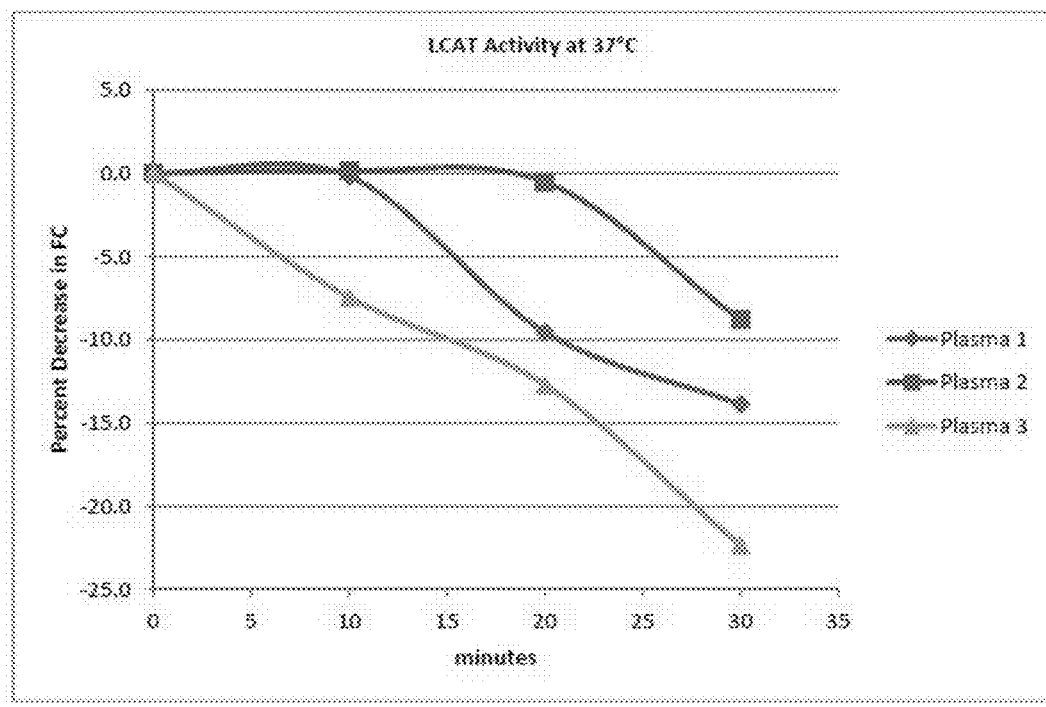

DETERMINATION OF LCAT

CROSS-REFERENCE TO RELATED APPLICATIONS

This application is a continuation of U.S. application Ser. No. 13/862,296 filed 12 Apr. 2013, which application claims priority to U.S. provisional Application Nos. 61/624,191 filed 13 Apr. 2012 and 61/642,337 filed 3 May 2012. The contents of the above patent applications are incorporated by reference herein in their entirety.

TECHNICAL FIELD

The invention relates to the field of blood tests, in particular to tests designed to detect cholesterol or lecithin:cholesterol acyltransferase (LCAT) activity. The methods take advantage of formation of complexes between cholesterol and macrolide antibiotics that can be quantified using optical spectra.

BACKGROUND ART

Measurement of cholesterol levels in plasma that are associated specifically with high-density lipoprotein (HDL) particles is of great interest in view of the *nexus* between cholesterol levels and cardiovascular problems. Current methods are typically based on enzymatic reactions. If total cholesterol (TC) is to be measured, which is a combination of free cholesterol (FC) and cholesterol ester (CE), three enzymes are typically used—cholesterol esterase, also known as cholesterol ester hydrolase (CEH), cholesterol oxidase and peroxidase along with reagents for detecting hydrogen peroxide.

When free cholesterol is measured in HDL or plasma, only two of these enzymes are used—cholesterol oxidase and peroxidase. Monitoring a change in free cholesterol concentration is routinely used to measure LCAT activity, which catalyzes conversion of free cholesterol to cholesteryl esters with acyl groups from phosphatidylcholine. Inhibitors of this enzyme, such as iodoacetate are often added to the LCAT assay reaction mixture to act as a negative control. Unfortunately, this also alters the activity of the enzymes cholesterol oxidase and/or peroxidase, critical to the free cholesterol assay.

Thus, for example, in a typical result using a commercially available enzyme-based assay employing cholesterol ester hydrolase, cholesterol oxidase and peroxidase and reagents to develop color, increasing the iodoacetate concentration from 0-250 mM lowers the estimated cholesterol content of a test solution containing 200 mg/dL of free cholesterol from 200 mg/dL when no iodoacetate is added to 175 mg/dL when 200 mM of iodoacetate is included in the reaction mixture. Clearly it would be advantageous to eliminate these artifacts.

It is known in the art that macrolide antibiotics—i.e., polyene, polyol macromolecules are able to complex with cholesterol to result in complexes that can be determined using optical spectroscopy by virtue of changes in their fluorescence spectra or optical density spectra. The present invention takes advantage of this complexation to assess the level of cholesterol in blood or plasma or fractions thereof, or in test samples generally.

DISCLOSURE OF THE INVENTION

In one aspect, the invention is directed to a method to determine the concentration of free cholesterol in a sample such as of plasma, serum, or fraction thereof, by contacting said sample with a macrolide antibiotic under conditions where the activity of lecithin:cholesterol acyltransferase (LCAT) is inhibited and measuring the level of fluorescence emitted upon formation of a complex. In particular, the FC and/or TC concentration can also be determined in HDL or apo-B containing lipoprotein. (Total cholesterol can be measured by adding cholesterol esterase to the reaction mixture.)

The invention also includes methods to determine the esterification rate of cholesterol in a sample, for example of plasma or serum as well as the level of LCAT activity in said sample by monitoring the time course of levels of free cholesterol taking advantage of the formation of the complex with the macrolide antibiotic. A similar assay may be used to determine cholesterol esterase (CEH) activity.

BRIEF DESCRIPTION OF THE DRAWINGS

FIG. 1 is a graph showing the comparison of LCAT activity in three different plasma samples at 37° C.

MODES OF CARRYING OUT THE INVENTION

The assays of the invention depend on the ability of macrolide antibiotics to form complexes with free cholesterol that fluoresce so that the fluorescence intensity may be used as a measure of the complex, and thus of the free cholesterol. The interaction of the macrolide with free cholesterol is very specific and cholesterol in the form of cholesterol esters does not form fluorescent complexes with these molecules. Thus, complexation with the macrolides makes a clear distinction between free cholesterol and cholesterol that is coupled to an acyl group.

As noted, for example, in an article by Bittman, R., et al., *PNAS* (1972) 69:3795-3799, the fluorescence excitation spectrum of nystatin is enhanced in the presence of increased concentrations of cholesterol without major modification of peak ratios and shape. The spectra were measured at various excitation wavelengths and detected at 400 nm for nystatin. However, when emission was detected at 480 nm for filipin and lagosin, decreases in emission intensity were found with excitation at 340 and 358 nm. Thus, the variation in fluorescence intensity on finding the macrolide antibiotics will depend on the antibiotic chosen and to some extent on the conditions of measurement.

The macrolides that are useful in the invention are described in an article by Hamilton-Miller, *JMT Bacteriol. Rev.* (1973) 37:166-196. Among the most useful among these are the tetranes nystatin, pimaricin, lucensomycin, and tetrin A and B, the pentanes chainin, filipin, and fungichromin (lagosin) and the heptanes amphotericin B, among others. As these are macromolecules, their solubility in water may be limited but can be improved by forming salts. These can be formed by first removing the amphoteric effects of a zwitterion formed by amino groups and carboxyl groups in these molecules. For example, the amino groups present in these compounds may be acetylated so that the carboxyl group also present can be provided as a salt, and conversely the carboxyl groups could be methylated, for example, using diazomethane permitting formation of the acid addition salts of the amino groups. In addition, the uptake of these molecules in water may be accelerated by agitation such as by mixing in a rotary flask in the presence of buffer and optionally in the presence of detergents such as deoxycholate. Methods to solubilize these molecules are well known in the art and suitable concentrations of the macrolide reagent may be prepared depending on the specific macrolide employed in the assay.

As stated above, all of the assays of the invention employ the formation of a complex of a macrolide with FC that alters the fluorescence of the macrolide antibiotic. Suitable excitation and emission wavelengths are dependent on the specific complex formed. While the primary interest of the applicants herein is determination of FC or related moieties in blood or plasma, the method of the invention is not limited to assessment of FC in these fluids, but is applicable to any fluid where the level of cholesterol is of interest. For example, the assay may also be used to monitor cholesterol concentrations in standard solutions or in reagents used in synthesis.

If there are no interfering substances in the sample to be analyzed, the assay for FC is straightforward—the macrolide reagent is simply mixed with the sample at a suitable pH, typically pH 5-8, although this may vary with the choice of macrolide, and the level of fluorescence is measured and compared to a standard or standard curve either determined concomitantly or previously determined with the results tabulated. If interfering materials are present, precautions may be necessary to obviate the effects of these interfering materials.

For example, if FC (or TC) is to be determined in a sample of serum or plasma LCAT present is a complicating factor because it is capable of converting FC to cholesterol ester (CE) with an acyl group derived from phosphatidylcholine. These interfering moieties may also be present even in preparations of HDL freed of LDL and VLDL. These are the samples where the levels of FC (and TC) are of most interest.

For determination of free cholesterol (FC), serum or plasma is first mixed with an inhibitor of LCAT, such as iodoacetate, an anti-LCAT antibody or aptamer, or, alternatively, the determination is carried out at a low temperature where LCAT activity is negligible. However, instead of this treatment, the fluorescence may be measured in sufficiently short time from mixing so that the interference from LCAT is negligible as well. If low temperature or the presence of the inhibitor is used, the sample may be incubated for several minutes or longer after mixing with the macrolide. Typically, the level of LCAT activity in serum or plasma is sufficient at 37° C. that a significant decrease in FC will be noted even after a few minutes, so it is preferable to inhibit this reaction in order to provide sufficient time to make the assay more practical. The fluorescence intensity output is then measured at the appropriate excitation and emission wavelengths to determine the level of FC. A standard or standard curve using known levels of cholesterol is used to compare. The standard curve or the comparative values may be determined concomitantly or on separate occasions and tabulated or otherwise presented to assess the level of FC. The standard or standard curve may also be run using comparable samples spiked with known amounts of FC. Alternatively, serum samples or plasma samples with known levels of FC may be used to prepare the necessary standards.

In order to determine the levels of cholesterol in high-density lipoprotein particles (HDL) the serum is first freed of very low-density lipoprotein (VLDL) and low-density lipoprotein (LDL) by precipitation of these particles as described in the "Preparation" section below herein. The general assay procedure is similar to that described above. On the other hand, the concentration of free cholesterol in LDL/VLDL may be measured directly in plasma without separating out HDL due to the affinity of the macrolide antibiotics for the lipoproteins associated with these components.

In more detail, in order to inhibit the activity of LCAT, a variety of methods may be used. First, regulating the temperature may sufficiently inhibit the activity to permit the assay to be run without an added inhibitor for practical purposes. Even at room temperature, apparently, the activity of LCAT is significantly decreased. Performing the assay at 4° C. or less essentially kills the activity of LCAT. Thus, one approach to eliminating this complication from the assay is to conduct the measurement of FC at temperatures below 25° C., preferably below 20° C. and more preferably below 15° C., 10° C. or 4° C.

In addition, or, generally, as an alternative, the assay may be conducted in the presence of an inhibitor of LCAT. Such inhibitors are known. Small molecule inhibitors include iodoacetate, 5,5-dithiobis-(2-nitrobenzoic acid) (DTNB, Ellman's reagent), p-chloromercuriphenyl sulfonic acid (PC-MPS); any colorless or essentially colorless small molecule that inhibits LCAT may be used in this reaction.

In addition, LCAT activity may be inhibited using specific binding macromolecules such as aptamers and antibodies. Antibodies, of course, include not only traditional complete antibodies, but also immunoreactive fragments, single-chain antibodies, recombinant antibodies and the like. Aptamers can be prepared to LCAT using known methods. Various other specific binding proteins or polymers may also be used.

These inhibitors are thus useful in order to extend the time that may lapse after addition of reagent to the sample before the fluorescence is measured.

In addition to measurement of FC, total cholesterol (TC) may also be measured in a sample by adding cholesterol ester hydrolase, i.e., cholesterol esterase to the sample in a sufficient amount to convert any cholesterol ester to free cholesterol. Typically, this assay is most useful in biological fluids as samples, especially serum or plasma or fractions thereof. For use in such assays, it may be desirable to add an inhibitor of LCAT as well since the cholesterol esterase will essentially be in competition with LCAT. As generalized inhibitors may inhibit cholesterol esterase as well as LCAT, such inhibitors should be specific to LCAT, such as antibodies or aptamers described above. Under certain conditions, however, sufficient cholesterol esterase may be added that, in comparison, the LCAT activity becomes insignificant.

In either case, specific inhibition of LCAT may be effected by removing the non-cholesterol substrate, phosphatidylcholine, from the sample, thus depriving the enzyme of a source of acyl groups. Materials are available that can capture phospholipids from serum; some materials pull about 99% of the phospholipids out of the serum or plasma. The phosphatidylcholine can thus be removed from the sample, for example, with $TiO_2$ $ZrO_2$ medium such as that available from Glygen Corporation.

Thus, in summary, in this first aspect, the invention is directed to a method to determine the level of FC and/or TC in samples, especially samples of serum, plasma or fractions thereof.

Another aspect of the invention is measurement of the activity of LCAT or cholesterol esterase. Cholesterol esterase (CEH) is not present in blood or serum, but may be present in other fluid samples. LCAT is prevalent in serum or plasma. In either case, the activity of these enzymes is measured by the change in level of FC using the assays as described above. It is also possible simply to measure the esterification rate of cholesterol without correlating the rate to LCAT activity or amount.

To determine the esterification or hydrolysis rate per se, the measurements described above are measured as a function of time. To be of interest, typically, this would be measured as esterification due to LCAT in serum or plasma under physiological conditions, e.g., 37° C. at generally neutral pH. The sample is contacted with macrolide reagent and the fluorescence levels as a function of time correlated to levels of cholesterol using the standards described above, or aliquots of the samples to be measured may be withdrawn at various timepoints and the macrolide antibiotics added to the aliquots to quantitate the fluorescence in each aliquot and thus obtain a measure of FC as a function of time.

For determination of LCAT activity in serum, plasma or fractions thereof, typically, parallel samples are used, one as a negative control either containing inhibitor or at a low temperature and the other as a test sample. Cholesterol levels are measured at at least one time interval, such as time zero to a time, for example, 20 minutes later, however, a more detailed picture may be obtained by measuring the cholesterol level at a plurality of timepoints. Thus, either the samples are incubated with the macrolide antibiotic and the fluorescence monitored at various timepoints, or the samples are simply incubated in parallel (preferably) and aliquots withdrawn, the macrolide antibiotic added to the aliquots, and the fluorescence measured in each aliquot. A multiplicity of timepoints is desirable, for example, after one or two or three or four 2 or 3-minute intervals.

If the level of cholesterol esterase is measured, the level of FC will increase and the fluorescence intensity at the appropriate excitation and emission wavelengths will increase with time when the macrolides pimaricin, nystatin or lucensomycin are used and decrease if filipin or lagosin is used. If LCAT is measured, the free cholesterol level will decrease with time and the fluorescence will decrease with time when the macrolides pimaricin, nystatin or lucensomycin are used and increase if filipin or lagosin is used The same inhibitors as those described above can be used in the assay for CEH or LCAT and a multiplicity of timepoints can be obtained. (In a CEH assay, if a negative control is desired, specific CEH inhibitors such as antibodies or aptamers may be used.) The determination of LCAT or CEH units of activity is then directly determined from the rate curve obtained. To translate this into concentrations of enzyme as opposed to activity, comparison to a standard activity curve of known amounts of enzyme would be employed.

The examples below describe one illustration of the conduct of such parallel assays.

Preparation A

Preparation of Supernatant Containing HDL Particles from Serum

Several methods are available to precipitate LDL and VLDL particles from the sample to obtain a supernate that contains HDL:

A. One milliliter of serum was mixed with 100 µl of a mixture of equal parts of 40 g/L sodium heparinate solution (156 USP units/mg) and 1 mol/L $MnCl_2$ solution. After 10 minutes, the samples were centrifuged for 15 minutes at 4,000 g. The supernatant was aspirated with a Pasteur pipette. When turbid, the supernatant was filtered through a 0.20 µm (average pore size) filter. FC is determined on the supernatant.

B. Phosphotungstate reagent was prepared by dissolving 40 g of phosphotungstic acid in distilled water. The pH of the solution was adjusted to 6.15 with 1 mol/L NaOH, and the reagent was diluted to 1 L with water. One milliliter of serum was mixed with 20 µl of the 2.5 mmol/L $MgCl_2$ solution (final concentration: 1.39 µmol of phosphotungstic acid and 50 µmol of $MgCl_2$ per milliliter of serum). After 15 minutes, the HDL fraction was isolated by centrifugation. FC is determined on the supernatant.

C. One milliliter of serum is mixed with 200 µl of PEG 6000 solution (45 g dissolved in 100 mL of 0.2 mol/L Tris-HCl buffer, pH 8.2). The final PEG 6000 concentration in serum is 75 g/L. After thorough vortex-mixing, incubation, and centrifugation, HDL supernatant is isolated. FC is determined on the supernatant.

D. Four hundred microliters of plasma is mixed with 20 µl dextran sulfate (mw=50,000) solution 20 g/L and 20 µl 1.0 mol/L $MgCl_2$. After 10 minutes at room temperature the samples are centrifuged at 1500×g for 30 minutes. FC is determined on the supernatant.

Preparation B

Solubilization of Pimaricin

To methylate carboxyl groups, a suspension of 5 g of pimaricin in 100 ml of absolute methanol is stirred while a 0.10 to 0.15 M solution of diazomethane (determined by esterifying a known quantity of acetic acid) in 100 ml of tetrahydrofuran is added slowly, so that the reaction does not become too vigorous, then at room temperature for 2 hours.

As the esterification preceded the methyl ester goes into solution during the first 5-15 minutes. Excess diazomethane is destroyed by adding a few drops of acetic acid until effervescence ceases, and the solution is filtered if necessary. Any solid collected is washed with a little fresh methanol. The filtrate is concentrated to 40 ml and the product is precipitated by addition of 200 ml of ether, centrifuged, washed with fresh ether (3×100 ml) and dried. The pimaricin is then dissolved in aqueous medium at low pH to form the acid addition salt.

Pimaricin is treated with a large excess (50 moles of acyl anhydride at room temperature for 1 hour to acylate the amino group. This results in liberating the carboxyl group contained in pimaricin so that it forms salts in the presence of mild base and becomes soluble.

The following examples are intended to illustrate but not to limit the invention.

Example 1

Determination of LCAT Activity in Plasma or Serum

An excess volume (100 µl) of plasma or serum was placed in two microfuge tubes. One tube was placed in a water bath at 37° C. and one tube was incubated on ice, after a sufficient incubation time (5 to 30 minutes) the tube incubated at 37° C. is moved to an ice bath and allowed to cool. Both tubes are vortexed and quickly spun down to collect any condensate.

A fluorescence compatible microplate was loaded with 195 µl of pimaricin/100 mM tris pH 7.4/3.75 mM sodium deoxycholate solution and 5 µl of each plasma sample was added to the wells. The plate was read in a fluorescence spectrophotometer at excitation 320 nm, emission 405 nm.

The results are shown in Table 1 from triplicate samples in deoxycholate incubated for 20 minutes.

TABLE 1

|  | Raw FIU 320/405 | | | Average | FIU change due to FC |
|---|---|---|---|---|---|
| Plasma 4° | 26987 | 27822 | 26789 | 27199 | 4307 |
| Plasma 37° | 22655 | 23120 | 22900 | 22892 | |

The decrease in fluorescence intensity in plasma at 37° C. is due to a decrease in free cholesterol resulting from LCAT activity in the sample converting FC to CE.

Example 2

Alternative LCAT Determination

In a fluorescent compatible microplate LCAT activity was determined in four different plasma samples A, B, C and D, 10 µl of 150 mM iodoacetate in 100 mM tris buffer was added to wells of column 1 and 10 µl 100 mM tris buffer was added to wells of column 2. Plasma (20 µl) was added to the wells of columns 1 and 2. The plate was sealed and incubated for 60 minutes at 37° C. After incubation, the plate was chilled on crushed ice. The cover was removed and 10 µl of 100 mM tris buffer added to columns 1 and 10 µl of 150 mM iodoacetate in 100 mM tris buffer was added to wells of column 2. 100 µl pimaricin solution (2 mg/100 ml) with 200 µl 10% triton/10 ml was added to all the wells. The plate was left at room temperature for 30 minutes and then read at 320 nm excitation 405 nm emission.

The results are shown in Table 2.

TABLE 2

|  | Column 1 (Control) | Column 2 (Test) | Change |
|---|---|---|---|
| Plasma A | 26644 | 20542 | 6102 |
| Plasma B | 25030 | 15192 | 9838 |
| Plasma C | 25909 | 20277 | 5632 |
| Plasma D | 26594 | 24133 | 2461 |

As shown in Table 2, the FC in column 2 which does not contain inhibitor is diminished over the 30-minute period as compared to column 1, due to the activity of the LCAT in the sample. Plasma B has the highest LCAT activity followed by Plasma A, Plasma C and Plasma D.

Using this method, LCAT activity levels in three different plasma samples were determined. As shown in FIG. 1, there are substantial differences in the rate at which cholesterol is taken up by LCAT in the three samples. Plasma 3 contains much higher activity than either Plasma 1 or Plasma 2.

The invention claimed is:

1. A method to determine the transferase activity of lecithin: cholesterol acyl transferase (LCAT) in a sample of plasma, serum or fraction thereof which method comprises:
   a) incubating, in a first suitable container, at a temperature where LCAT activity that converts free cholesterol (FC) to a cholesterol ester is exhibited, a first sample from said plasma, serum or fraction thereof with pimaricin so as to form a complex with FC, which complex exhibits an intensity of fluorescence upon excitation greater than that of free pimaricin for a period of time starting at time zero and ending at a later time point;
   b) incubating, in a second suitable container, a second sample of said plasma, serum or fraction thereof with said pimaricin at a temperature where LCAT is inactive or in the presence of an LCAT inhibitor for said period of time;
   c) quantitating, in each of said first and second containers, fluorescence intensity at a plurality of time points occurring during said time period between time zero and said later time point and determining a decrease in concentration of FC in the first sample as a function of time;
   d) comparing the decrease in concentration of FC in said first sample as a function of time based on said quantitating at said time zero, said plurality of time points and said later time point to any decrease in concentration of FC of the second sample as a function of time;
   wherein a greater decrease in the concentration of FC in the first sample over that in the second sample is a measure of the activity of LCAT in the serum, plasma or fraction thereof.

2. The method of claim 1 wherein the inhibitor is iodoacetate, an anti-LCAT antibody or an aptamer specific for LCAT.

3. The method of claim 1 wherein the time period starts at time zero and ends at a time point 20 minutes later.

4. A method to determine the transferase activity of lecithin: cholesterol acyl transferase (LCAT) in a sample of plasma, serum or fraction thereof which method comprises:
   a) incubating, in a first suitable container, at a temperature where LCAT activity is exhibited, a first sample from said plasma, serum or fraction thereof with pimaricin so as to form a complex with FC which complex exhibits an intensity of fluorescence upon excitation greater than that of free pimaricin for a period of time starting at time zero and ending at a later time point;
   b) incubating in a second suitable container, a second sample of said plasma, serum or fraction with said pimaricin at a temperature where LCAT is inactive or in the presence of an LCAT inhibitor for said period of time;
   c) quantitating in each of said first and second containers the intensity of fluorescence at a plurality of time points occurring during said time period between time zero and said later time point in each of said first and second samples;
   wherein a greater decrease in intensity of fluorescence in the first sample over that in the second sample is a measure of the activity of LCAT in the serum, plasma or fraction.

* * * * *